United States Patent [19]

Knollmueller et al.

[11] 4,375,420
[45] Mar. 1, 1983

[54] SELECTED 4-HYDROXYPHENYL ANILINO ALKOXYSILANES AND THEIR USE AS ANTIOXIDANTS

[75] Inventors: Karl O. Knollmueller, Hamden; Theodore H. Fedynyshyn, Branford, both of Conn.

[73] Assignee: Olin Corporation, New Haven, Conn.

[21] Appl. No.: 350,690

[22] Filed: Feb. 22, 1982

[51] Int. Cl.³ .......................... C07F 7/10; C07F 7/18; C09K 5/00
[52] U.S. Cl. ................................... 252/78.3; 556/425
[58] Field of Search ....................... 556/425; 252/78.3

[56] References Cited

U.S. PATENT DOCUMENTS

| | | | |
|---|---|---|---|
| 2,762,823 | 9/1956 | Speier | 556/425 |
| 2,998,406 | 8/1961 | Bailey et al. | 556/425 X |
| 3,087,909 | 4/1963 | Lewis et al. | 556/425 X |
| 3,171,851 | 3/1965 | Pepe | 556/425 X |
| 3,249,535 | 5/1966 | Keil | 556/425 X |

OTHER PUBLICATIONS

B. F. Goodrich Chemical Company Material Safety Data Sheet for Good-Rite ™, (dated Sep. 1980).
Synopsis of Olin Corporation's U.S. Patents Relating to Silicate Cluster ™, Shielded Polysilicate Compounds and Methods of Their Preparation and Use.
R. C. Gunderson and A. W. Hart, Synthetic Lubricants, Reinhold Publishing Corp., New York, (1962), pp. 11–14, 302–306, and 341.
R. E. Hatton, Introduction to Hydraulic Fluids, Reinhold Publishing Corp., New York, (1962), pp. 163–167.
Chemical Abstracts: 77:34691f; 93:134151d; 93:169202y; 93:169035w; and 93:96489k.

Primary Examiner—Paul F. Shaver
Attorney, Agent, or Firm—William A. Simons; Thomas P. O'Day

[57] ABSTRACT

Disclosed are selected 4-hydroxyphenyl anilino alkoxysilanes of the formula:

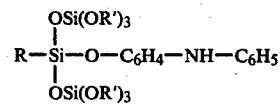

wherein R is hydrogen or a lower alkyl group having from 1 to 4 carbon atoms and each R' is individually selected from an alkyl group having 3 to 12 carbon atoms with the proviso that at least a majority of said R' radicals are sterically hindered alkyl groups. The compounds are disclosed to be effective antioxidants, especially in functional fluids having shielded polysilicate compounds, silicate esters, or silicone oils as base fluids.

13 Claims, No Drawings

SELECTED 4-HYDROXYPHENYL ANILINO ALKOXYSILANES AND THEIR USE AS ANTIOXIDANTS

BACKGROUND OF THE INVENTION

1. Field of the Invention

The present invention relates to a novel class of antioxidants which are useful in functional fluids, particularly those which have shielded polysilicate compounds, silicate esters, or silicone oils as base fluids. More specifically, the present invention relates to the use of selected 4-hydroxyphenyl anilino alkoxysilanes as these antioxidants.

2. Description of the Prior Art

Antioxidants are widely used in many functional fluids, including those that have hydrocarbon fluids, silicate esters, and silicones as base fluids. They are used to prevent oxidation from degrading the fluid and, thereby, decreasing its performance.

It is generally believed that oxygen acts upon organic compounds, including functional fluids, by a free radical mechanism. These radicals may be initiated by thermal or mechanical cleavage of molecules in the functional fluid. Then, these radicals combine readily with oxygen to give peroxy radicals which then react in a number of ways depending upon the environment and the type of compound. The ultimate products may be ketones, alcohols, and carboxylic acids that may condense to polymer chains such as lacquers, gums, sludges, and the like. These latter materials may be corrosive or remain in the fluid, thereby increasing the viscosity of the fluid above operational levels. Conversely, cleavage products may form which reduce viscosity and increase volatility to unacceptable levels.

Antioxidants are used to prevent this oxidation process by reacting with the radicals before they form the polymer chains. Therefore, the propagation of polymer chains is inhibited and the properties of the functional fluid will change by a lesser amount, if at all, over a period of time.

Functional fluids having either shielded polysilicates, silicate esters, or silicone oils or mixtures thereof as base fluids have special problems in protecting them against oxidation because they tend either to form gels upon oxidation or to have a limited solubility, stability, or efficiency for most common additives in general and most common antioxidants in particular. Accordingly, there is need to find new antioxidants which may be easily used with many types of functional fluids, including shielded polysilicate compounds, silicate esters, and silicone oils.

BRIEF SUMMARY OF THE INVENTION

The present invention, therefore, is directed to selected 4-hydroxyphenyl anilino alkoxysilanes as novel compositions of matter. These compounds have the formula (I):

$$\begin{array}{c} OSi(OR')_3 \\ | \\ R-Si-O-C_6H_4-NH-C_6H_5 \\ | \\ OSi(OR')_3 \end{array} \quad (I)$$

wherein R is hydrogen or a lower alkyl group having from 1 to 4 carbon atoms and each R' is individually selected as an alkyl group having from 3 to 12 carbon atoms, with the proviso that at least a majority of said R' radicals are sterically hindered alkyl groups. The present invention is also directed toward the use of these compounds as antioxidants in functional fluids.

DETAILED DESCRIPTION

The 4-hydroxyphenyl anilino alkoxysilanes of the present invention may be prepared by reacting the corresponding halo-(bis-trialkoxysilyloxy) alkyl silane (of the formula R-Si[OSi(OR')$_3$]$_2$X wherein R and R' are defined above and X is a halogen) with 4-hydroxyphenyl aniline in the presence of a suitable solvent and acid scavenger. This general reaction is illustrated by the following Equation (A) wherein chloro-[bis(tri-sec-butoxysilyloxy)]-methyl silane is reacted with 4-hydroxyphenyl aniline in toluene and pyridine to produce the desired 4-hydroxyphenyl anilino alkoxysilane:

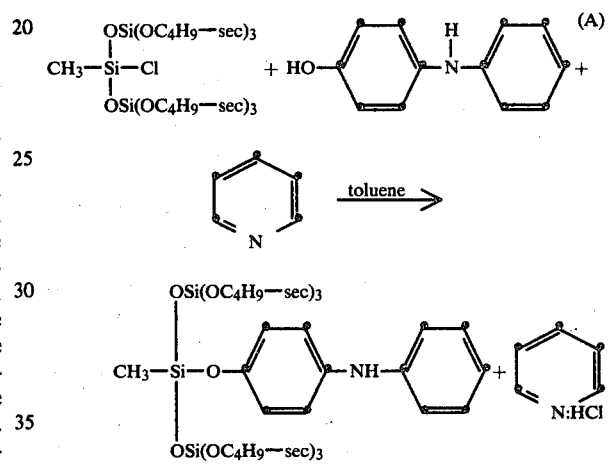

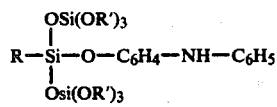

The halo(bis-trialkoxysilyloxy) alkyl silane reactants and their synthesis are disclosed in U.S. Pat. No. 3,960,913, which issued to K. Knollmueller on June 1, 1976, and is incorporated herein by reference in its entirety. These reactants may be made and isolated before being reacted with 4-hydroxyphenyl aniline to make the compounds of the present invention. Alternatively and preferably, it is desirable to make these reactants from the corresponding trialkoxysilanol [HOSi-(OR')$_3$] and trihalosilane [R-SiX$_3$] and then adding the 4-hydroxyphenyl aniline to the reaction mixture without any isolation step. This technique simplifies the synthesis and may prevent loss of the reactant.

The preferred examples of these halo-bis(trialkoxysilyloxy) alkyl silane reactants have an R radical which is a lower alkyl group having 1 to 4 carbon atoms. The most preferred example has an R radical which is methyl. The preferred halo-radical for this reactant is chloro. The preferred examples of these reactants have R' radicals which are individually selected from alkyl groups having 4 to 10 carbon atoms, subject to the proviso that at least a majority of the R' radicals are sterically hindered alkyl groups. More preferably, all of the R' radicals of this reactant are sterically hindered alkyl groups having about 4 to about 10 carbon atoms. Most preferably, all of the R' radicals are sterically hindered alkyl groups derived from secondary or tertiary alcohols and having from about 4 to about 10 carbon atoms. A specific example of the most preferred R' radical is a sec-butyl group. The preferred compound of this class of reactants is chloro[bis(tri-sec-butoxysilyloxy)]-methyl silane as shown in Equation (A) above.

Sterically hindered alkyl groups are defined as alkyl radicals which contribute to the hydrolytic stability of the molecule, i.e., which inhibit the reaction of water with silicon-oxygen or the carbon-oxygen bonds in the molecule. Exemplary of preferred sterically hindered alkyl R' radicals include (1) non-linear primary alkyl radicals having a beta position side chain of at least 2 carbon (e.g., iso-butyl, 2-ethyl butyl, 2-ethyl pentyl, 3-ethyl pentyl, 2-ethyl hexyl, 2,4-dimethyl-3-pentyl, and the like); (2) secondary alkyl radicals (sec-butyl and the like); and (3) tertiary alkyl radicals (tert.-butyl,1,1-dimethylpropyl and the like).

Another alternative synthesis approach is to use an alkoxysilane cluster amide of the formula R-Si[O-Si(OR')$_3$]$_2$(N-R''R''') where R and R' are as defined above and R'' and R''' are individually selected from hydrogen, lower alkyl groups having 1-4 carbon atoms, and phenyl. Such an alkoxysilane cluster amide would be used as a reactant for the compounds of the present invention instead of the corresponding halo-(bis-trialkoxysilyoxy) alkyl silane. These amide reactants and their synthesis are disclosed in U.S. patent application No. 278,225 filed by K. Knollmueller on June 29, 1981. This patent application is incorporated herein by reference in its entirety.

The other reactant for the compounds of the present invention is 4-hydroxyphenyl aniline (also known as p-hydroxydiphenylamine, p-anilinophenol, or 4-hydroxy-N-phenylaniline). This reactant is commercially available. One current source is the B. F. Goodrich Chemical Company of Cleveland, Ohio, which sells this chemical under the name Good-rite® 3920X3 Antioxidant. Alternatively, this reactant may be made by reacting para-hydroquinone with aniline in the presence of CaCl$_2$ and a catalytic amount of H$_2$SO$_4$.

Any conventional reaction conditions designed to produce 4-hydroxyphenyl anilino alkoxysilanes may be employed in the synthesis of the present compounds and the present invention is not intended to be limited to any particular reaction conditions. Advantageously and preferably, the present compounds may be made according to the reaction illustrated in Equation (A) in the presence of an inert solvent such as toluene and an acid acceptor like pyridine.

The mole ratio of the 4-hydroxyphenyl aniline to halo-bis(trialkoxysilyloxy) alkyl silane compound as reactant is preferably at least about 0.8:1 to ensure a desired yield of the desired antioxidant product. More preferably, this mole ratio is in the range of about 0.9:1 to about 1.3:1.

The use of a solvent or an acid acceptor, or both, is only desirable and not necessary. Both the reaction temperature and time will depend upon many factors including the specific reactants and apparatus employed. In most situations, reaction temperatures from about 25° C. to about 200° C. may be employed. The reaction temperatures for the reaction illustrated by Equation (A) are preferably from about 40° C. to about 120° C. Reaction times from about 30 minutes to about 1440 minutes may be employed. The reaction times will also depend upon the reaction temperatures chosen. The reaction pressure is preferably atmospheric; although subatmospheric (e.g., down to about 200 mm Hg) and superatmospheric (e.g., up to 10 atmospheres) pressures may be useful in some situations. The desired products of the present invention may be removed from the reaction mixture by any suitable means, including evaporation of the solvent, filtration, extraction, recrystallization, distillation, or the like.

It should be noted that while the reaction illustrated by Equation (A) is the preferred method for preparing the compounds of the present invention, other synthetic methods may also be employed.

Also, in accordance with the present invention, the compounds of Formula I, above, may be utilized as effective oxidation inhibitors or antioxidants. In practicing the process of the present invention, an effective oxidation-inhibiting amount of one or more of these compounds is added to a functional fluid. It is understood that the term "effective oxidation-inhibiting amount" as used in the specification and claims herein is intended to include any amount that will prevent or control the oxidation of said functional fluid. Of course, this amount may be constantly changing because of the possible variations in many parameters. Some of these parameters may include the specific base fluid to be protected; the salt and oxygen content of the system; the specific compound of the present invention used as an antioxidant; the geometry and capacity of the system to be protected; temperature; and the like.

The compounds of this invention may be preferably used in concentrations ranging from about 0.05% to about 10% by weight of the functional fluid composition. Functional fluids in which the compounds of the present invention may be suitable include hydrocarbon distillate fuels, lubricant oils and greases, and non-hydrocarbon (i.e., synthetic oil base stocks) distillate fuels, lubricant oils and greases. The latter may include phosphate esters, carbonate esters, silicones, silicate esters, alkoxysilane cluster compounds, polyglycols, glycol esters and the like. These functional fluids may be used as fuels, lubricating oils, hydraulic fluids, brake fluids, heat transfer fluids, and the like.

One preferred functional fluid base fluid is shielded polysilicate compounds. This class of compounds includes the subgroups of alkoxysilane cluster compounds, alkoxysilanol cluster compounds, halogenated alkoxysilane cluster compounds, alkoxysilane multiple cluster compounds, and silicone bridged alkoxysilane double cluster compounds. Such compounds and their preparation are more fully described in commonly assigned U.S. Pat. Nos. 3,960,913; 3,965,135; 3,965,136; 3,992,429; 4,058,546; 4,077,993; and 4,086,260. The disclosures of all of these respective patents hereby are incorporated by reference in their entireties.

The use of alkoxysilane cluster compounds, alkoxysilane multiple cluster compounds, and silicone bridged alkoxysilane double cluster compounds (more fully described in U.S. Pat. Nos. 3,965,136; 3,992,429; and 4,058,546, respectively) is preferred. Alkoxysilane cluster compounds are particularly preferred. These alkoxysilane clusters have the general formula:

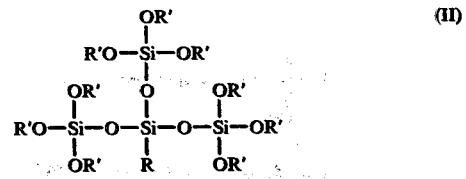

wherein R is hydrogen, alkyl, alkenyl, aryl, or aralkyl and each R' is independently selected from the same group as R with the proviso that at least a majority of R' radicals on each Si are sterically hindered alkyl groups having at least 3 carbon atoms.

Desirably, R is hydrogen, an alkyl or alkenyl having about 1 to about 18 carbon atoms or an aryl or aralkyl having about 6 to about 24 carbon atoms. Preferably, R is hydrogen, an alkyl having from 1 to about 8 carbon atoms or an aryl or aralkyl having about 6 to about 14 carbon atoms. In Formula (II), each R' is independently selected from the same group as R, with the proviso that at least a majority of the R' radicals are sterically hindered alkyl groups having at least 3 carbon atoms. The desired and preferred groups for R' are the same as for R subject to the preceding proviso. Desirably, at least a majority of the R' radicals are sterically hindered alkyl groups having about 3 to about 24 carbon atoms and preferably are sterically hindered alkyl groups having about 4 to about 12 carbon atoms. By sterically hindered alkyl groups is meant alkyl radicals which contribute to the hydrolytic stability of the molecule, i.e., which inhibit the reaction of water with the silicon-oxygen or the carbon-oxygen bonds in the molecule. Exemplary of sterically hindered alkyl radicals are non-linear primary alkyl radicals having a beta position side chain of at least 2 carbon atoms, secondary alkyl radicals and tertiary alkyl radicals. Particularly useful sterically hindered alkyl groups include sec. butyl, isobutyl, 2-ethyl butyl, 2-ethyl pentyl, 3-ethyl pentyl, 2-ethyl hexyl, 3-ethyl hexyl, 2,4-dimethyl-3-pentyl, and the like.

Another preferred class of functional fluid base fluid that may be used with the antioxidant of the present invention is silicone oils. Conventional silicone oils include polydimethyl silicones, polyphenylmethyl, silicones, polychlorophenylmethyl silicones, polytrifluoropropyl silicones, and the like. Such oils are prepared from organo-silicon compounds by methods well known in the art. Polydimethyl silicones, for example, which are preferred, commonly are formed by controlled hydrolysis and polymerization of dimethyldichlorosilane to form a controlled molecular weight water-insoluble oily polymer.

One preferred use for the antioxidants of the present invention is in diffusion pump fluids. For example, a diffusion pump fluid may comprise a shielded polysilicate compound or a silicone oil as a base fluid and an effective oxidation-inhibiting amount of one or more of the compounds of Formula (I).

There are various other inhibitors and additives that are commonly known in the functional fluid art that can be employed in the presently described fluid composition to further control or modify various chemical and physical properties of the fluids. The general term "inhibitor" is used for those additives which increase resistance to chemical changes. The ultimate function of an inhibitor is to maintain both the mechanical parts of the system and the fluid as close to their original conditions as possible.

Included among the various types of other additives which can be added to the functional fluids of this invention are: inhibitors for pH and corrosion control, other antioxidants, rust inhibitors, viscosity-index improvers, pour-point depressants, wear additives, lubricating additives, anti-foamants, stabilizers, demulsifiers, dyes, and odor suppressants. Generally, the total amount of additives which may be incorporated into the fluid composition will vary depending on the particular composition and the desired properties. More particularly, the total amount of other additives will comprise from 0 to 20 percent and preferably from 0.1 to 8.0 percent by weight based on the total weight of the fluid composition.

A wide range of materials are of known utility as antioxidants, and any of these may be used with the compositions of the present invention. Known antioxidants include phenolic compounds, such as 2,2-di-(4-hydroxyphenyl)-propane, phenothiazine, phenothiazine-carboxylic acid esters; N-alkyl or N-arylphenothiazines such as N-ethyl-phenothiazine, N-phenylphenothiazine, polymerized trimethyldihydroquinoline; amines, such as phenyl-alphanaphthylamine, dioctyl diphenylamine, p-isopropoxydiphenylamine, N,N-dibutyl-p-phenylene diamine, diphenyl-p-phenylenediamine, N,N'-bis(1,4-dimethylpentyl)-p-phenylenediamine, N,N'-diisopropyl-p-phenylene-diamine, p-hydroxydiphenylamine; hindered phenols such as dibutyl cresol, 2,6-dimethyl-p-cresol, butylated 2,2-di-(4-hydroxyphenyl)-propane, n-butylated aminophenol, butylated hydroxyanisoles, such as 2,6-dibutyl-p-hydroxyanisole; anthraquinone, dihydroxy-anthraquinone, hydroquinone, 2,5-di-tertiary butylhydroquinone, 2-tertiary butylhydroquinone, quinoline, p-hydroxydiphenylamine, phenyl benzoate, p-hydroxy-anisole, pyrocathechol, styrenated phenol, and polyalkylpolyphenols.

Inhibitors for corrosion control can also be employed. These inhibitors are generally added in an amount of from 0.01 to 8.0 percent by weight based on the total weight of the fluid composition and preferably from 0.2 to 6.0 percent by weight on the same basis. Useful inhibitors include salicylylmonoethanolamine, di-$\beta$-naphthyl-p-phenylene-diamine, N,N'-disalicylidene-1,2-propanediamine, N,N'-disalicylylethylene-diamine; phosphites, such as triphenyl phosphite, tri(tertamylphenyl) phosphite, diisopropyl phosphite; mercaptobenzotriazole; triazoles including benzotriazole 1,2-naphthotriazole, 4-nitrobenzotriazole, tolutriazole; aminobenzotriazoles such as 5-acylaminobenzotriazole, and alkyl-triazoles having 1 to 10 carbon atoms in the alkyl group as exemplified by methyl-triazole, ethyl-triazole, n-propyl-triazole, tertiary-butyl-triazole, hexyltriazole, isodecyl-triazole. Other useful corrosion inhibitors include adenine, 4-methylimidazole, 3,5-dimethyl-pyrazole, 6-nitroimidazole, imidazole, benzimidazole, indazole, ammonium dinonylnaphthalenesulfonate, diolyl thiodipropionate, ethyl benzoate, ethyl p-aminobenzoate, 4,4'-methylene-bis(2,6-di-tert-butylphenol), 4-hydroxymethyl-2,6-di-tertbutylphenol, 4,4'-methylene-bis(4-methyl-6-tert-butylphenol), salicylyl-o-aminophenol, 2,6-di-tert-butyl-2-dimethylamino-p-cresol, 4,4'-thiobis-(6-tert-butyl-o-cresol). Mixtures of the above inhibitors can be employed if desired.

An important class of inhibitors used in functional fluids are rust inhibitors. Rust preventative additives consist of polar compounds capable of being absorbed at the metal-fluid interface. These additives generally include: esters such as sorbitan monooleate, barium petroleum sulfonate, butyl stearates, butyl naphthenates; nitrogen compounds such as amines and amides; phosphorus compounds, such as phosphorus acid esters; and metal soaps, such as aluminum stearate. These rust inhibitors generally are used in an amount ranging from about 0.01 to about 10 percent; preferably from about 0.1 to about 2 percent.

Lubricating additives may also be included in the present compositions. These additives are often classified into three indistinct overlapping groups: extreme pressure agents, anti-wear agents, and lubricity agents.

Such additives are represented by sulfur-containing compounds, reactive halogen-containing compounds, and phosphorus-containing compounds. Typical representatives include zinc dialkylphosphorodithionates, phosphate esters, phospho-sulfurized fats and hydrocarbons, chlorinated kerosenes and waxes, xanthates, sulfides and trithiocarbonates. These lubricity additives generally are employed in an amount ranging from about 0.1 to about 10 percent; preferably about 0.2 to about 2.0 percent.

The above-noted inhibitors and additives are merely exemplary and are not intended as an exclusive listing of the many well-known materials which can be added to functional fluid compositions to obtain various desired properties. Numerous additives useful in hydraulic fluids are disclosed in *Introduction to Hydraulic Fluids* by Roger E. Hatton, Reinhold Publishing Corp., (1962).

The following Examples illustrate various embodiments of the present invention. All parts and percentages are by weight unless explicitly stated otherwise.

EXAMPLE 1

PREPARATION OF
BIS(TRI-SEC-BUTOXY-SILYLOXY)P-ANILINO
PHENOXY-METHYL SILANE $H_3C-Si[OSi(OC_4H_9sec)_3]_2-OC_6H_4NHC_6H_5$ A three neck flask of 500 ml capacity was equipped with a stirrer, reflux condenser, thermometer, and equilibrated dropping funnel, which was also used to admit a dry nitrogen purge to the system. To prevent air or moisture from entering the system, an oil bubbler was attached to the reflux condenser to monitor the nitrogen flow. The reaction flask was charged with 18.52 g. 4-hydroxy diphenylamine of the formula $HOC_6H_4NHC_6H_4$ (0.1 mole), 7.9 g. pyridine (0.1 mole), and 100 ml toluene. The dropping funnel held a charge of 63.1 g. chloro-bis(tri-sec-butoxy-silyloxy)-methyl silane of the formula $H_3CSi[OSi(OC_4H_9sec)_3]_2Cl$. It showed a VPC assay of 95.9% which represents a charge of 60.54 g. active material or 0.1 mole. While the stirred reaction mixture was kept at +2° to 4° C., the contents of the dropping funnel were added over a 50 minute period. After completion of the addition, the reaction mixture was heated to 50° C. and kept there overnight. The solution was then cooled to 2° C. and filtered. The brown solids consisted of pyridine hydrochloride, coagulated with tarry co-products or unreacted 4-hydroxy diphenylamine. The solids were washed with 100 ml. toluene. The combined filtrate and wash was vacuum stripped, leaving a dark brown liquid.

Fractionation through a micro Vigreux column and a short path apparatus afforded dark brown forecuts and a light brownish main fraction which boiled at 222°–227° C. and 0.04 mm Hg. The assay by VPC was 99.7% and analytical data were as follows:

| | Calculated for $C_{37}H_{67}NO_9Si_3$: | | |
|---|---|---|---|
| C = 58.92% | H = 8.96% | N = 1.86% | Si = 11.17% |
| | Found | | |
| C = 57.45% | H = 8.58% | N = 2.00% | Si = 11.24% |

The yield was 59.4%. The product was stored over $N_2$ in a crimp vial. Exposure to air during a withdrawal changed the color to a slight red-purple. This did in no way affect the inhibitor potential.

EXAMPLE 2

This example shows the synthesis via the alternate route, using previously prepared $H_3C-Si[OSi(OC_4H_9sec)_3]_2-N(CH_3)_2$.

A 100 ml flask was equipped with a magnetic stirrer, a gas inlet tube, and a small reflux condenser. The flask was charged with 8.94 g. N,N-dimethyl amido-bis(tri-sec-butoxy-silyloxy)methyl silane of the formula $H_3C-[OSi(OC_4H_9sec)_3]_2-N(CH_3)_2$, assay 93% by VPC, which was a charge of 8.4 g. active material of 0.0137 mole. To it was added 2.53 g. 4-hydroxy diphenylamine of the formula $HOC_6H_5NHC_6H_5$ (0.0137 mole). While passing a slow stream of dry $N_2$ through the system, it was heated in an oil bath for 3 hours to 125° C. and 2 hours to 140° C. after which time the dimethylamine evolution ceased. The crude material weighed 10.07 g. and the VPC assay was 74.7% which is a yield of 72.8%.

EXAMPLE 3

This example demonstrates the large scale preparation of $H_3C-Si[OSi(OC_4H_9sec)_3]_2 OC_6H_4NHC_6H_5$ and the synthesis without isolation of the intermediate $H_3C-Si[OSi(OC_4H_9sec)_3]_2 Cl$.

A 2 liter three neck flask was equipped with a stirrer, reflux condenser, thermometer, and an equilibrated dropping funnel through which reagents could be added and which served also to introduce and maintain a nitrogen blanket over the reactants.

The flask was charged with 121.5 g. methyltrichlorosilane of the formula $H_3C-SiCl_3$ (0.813 mole) dissolved in 200 ml toluene. This stirred mixture was cooled to 2° to 5° C. Into the large dropping funnel was placed the following mixture: 900 g. of a solution containing 47.76% tri-sec-butoxy-silanol in toluene, which is 429.84 g. (sec $C_4H_9O)_3SiOH$ or 1.626 mole. To this solution in the dropping funnel was added 250 g. pyridine or 3.16 mole. The silanol/pyridine/toluene mixture was now dropped to the methyltrichlorosilane over a 2½ hour period, during which time the reaction temperature was allowed to rise from 2° to 22° C. The reaction mixture was after 20 minutes checked by VPC to ensure that a maximum of chloro(bis-tri-sec-butoxy-silyloxy)-methyl silane intermediate was present. A solution of 150 g. 4-hydroxy diphenylamine of the formula $HOC_6H_4NHC_6H_5$ (0.813 mole) in 250 ml hot toluene was now made up and added rapidly to the reaction mixture. It was heated to 60° C. and held overnight.

A VPC showed that 67% by weight of the desired product was present (on a solvent free basis) and that the chloro-ester intermediate had disappeared.

The cooled reaction product was washed 5 times with 500 ml water to remove pyridine hydrochloride and dark co-products (soluble tars). After drying over $MgSO_4$ and filtration, the toluene solvent was vacuum stripped. The crude product was vacuum fractionated using a Vigreux column. During the early part of the fractionation unreacted 4-hydroxy diphenylamine distilled with co-products and the condenser had to be heated to prevent solidification and clogging.

The portion of the distillate containing the product was refractionated in vacuo on a Vigreux column. The pure product was 99.8 to 100% VPC purity distilled at 230°–234° C./0.07–0.1 mm Hg and weighed 306 g. which represents a 50% in hand yield.

The properties of the product were identical to the one prepared in Example 1.

EXAMPLE 4

A system was set up to test the inhibitor in diffusion pump oils. It consisted of a rotary forevacuum pump, protected by a dry ice trap followed by a pneumatically operated butterfly valve. It in turn was connected to a one-stage glass air-cooled oil diffusion pump, the heater of which was a resistance wire spiral immersed in the fluid. The diffusion pump was connected to a manifold which held a cold cathode gauge for measuring the pressure. To the manifold was also connected a solenoid valve to admit dried air to the system. A timer could hold the system in two states. In the operation mode the vent valve was closed, the butterfly valve open, and power was supplied to the pump. In the vent mode the butterfly valve was closed, simultaneously cutting power to the heater and opening the vent valve. In normal testing the operation mode was on for 21 minutes followed by three minutes vent node. The cycle would then repeat. In a 24 hour period, 58 cycles could thus be completed.

The operational part of the cycle could be manually overridden to lengthen pumping time. This was done daily to measure the ultimate vacuum obtainable.

The pressure was measured on a cold cathode gauge to room temperature and using a dry ice trap on the connecting line to the gauge. There were provisions to monitor the pump fluid temperature by a thermocouple and a strip chart recorder.

The diffusion pump was filled with 60.1 g. tris(tri-sec-butoxy-silyloxy)-methyl silane of the formula $H_3C$-$Si[OSi(OC_4H_9sec)_3]_3$ to which was added 0.3 g. inhibitor from Example 1 (0.5% inhibitor level). The system was now operated for 23 days or 1350 of the cycles described. The ultimate pressure achievable with this system stayed constant throughout the experiment and was $1 \times 10^{-6}$ mm Hg (untrapped) and between 2.5 and $5 \times 10^{-7}$ mm Hg (trapped with dry ice). No decomposition products of the fluid were found in the trap which contained only misted-over traces of the fluid. The color of the fluid had changed from almost colorless to light brownish; no differences could be seen by VPC from the starting material and the product which had undergone the test.

COMPARISON 1

As a control, Example 4 was run without the antioxidant of the present invention. Instead, the fluid was inhibited by two commercial antioxidants, Ethyl 330[1] and Irganox L109[2], at 0.05% by weight each (this is the solubility limit of both antioxidants in the fluid at room temperature).

[1]Ethyl 330 is 1,3,5-trimethyl-2,4,6-tris[3,5-di-tert-butyl-4-hydroxybenzyl]benzene and is manufactured by Ethyl Corporation, Industrial Chemicals Division, Baton Rouge, La.
[2]Irganox L109 is a high molecular weight (m.w. of 640) phenolic oxidation inhibitor for lubricating oils and greases made by Ciba-Geigy Corporation of Ardsley, N.Y.

After 300 cycles, giving pressures as described in Example 4 up to then, the achievable ultimate vacuum began to deteriorate.

After 750 cycles, the achievable pressure was $1 \times 10^{-5}$ mm Hg untrapped and 5 to $8 \times 10^{-6}$ mm Hg trapped.

The experiment was terminated at 1200 cycles. As measured by VPC, only 76.7% by weight of the fluid was undecomposed tris(tri-sec-butoxysilyloxy)-methyl silane; 19.6% of the weight of the original charge was found in the trap as a mixture of sec butanol, butanone acetic acid, and butyl acetate. The fluid also contained polymers, presumably formed during oxidative decomposition, which could only be seen by gel permeation chromatography. Comparing the results of Example 4 to Comparison 1, one can see that the antioxidant of the present invention was superior to commercially-known antioxidants when used in an alkoxysilane cluster base fluid.

EXAMPLE 5

OXIDATIVE STABILITY TEST

A 100 ml flask was outfitted with a connecting head which consisted of an air bubbler tube, a thermowell tube, and a connecting tube with a ground joint, connected to a small trap cooled with dry ice. The trap had a conical bottom and a stopper on the center delivery tube. Through the stoppered opening a syringe could be inserted and samples from the conical bottom collected for analysis by VPC.

The flask was charged with 60.8 g. tris(tri-sec-butoxy-silyloxy)-methyl silane of the formula $H_3C$-$Si[OSi(OC_4H_9sec)_3]_3$ inhibited with 0.5% by weight $H_3C$-$Si[OSi(OC_4H_9sec)_3]_2$-$O$-$C_6H_4NHC_6H_5$ from Example 1. Dry air was bubbled through the system at a rate of 236 ml/min. (0.5 ft$^3$/hr.) while the system was heated to 185° C. and maintained there within ±1° C. by a temperature controller.

The trap contents were analyzed daily by VPC and weighed. During the 103 hours of operation, the oxidized inhibitor turned the color of the fluid red. But cumulative, only 0.13 g. or 0.21% of oxidation products were seen in the trap. The bulk weight of the trap contents was 2.27 g. (cumulative) and consisted of misted fluid carried over by the bubbling. The fluid increased in viscosity from 59.33 cst to 63.34 cst at 24° C. which is a 6.7% increase over 103 hours.

COMPARISON 2

This was the control experiment, using the equipment and conditions as described in Example 5 but uninhibited tris(tri-sec-butoxy-silyloxy)-methyl silane fluid.

After 16 hours, 24.8% of the material was volatized; of this material in the trap, 98.9% by weight consisted of oxidation products mentioned in Example 5. The viscosity had increased from 59.33 cst to 895.6 cst at 24° C., which is a 1409% increase. Comparing the increase in viscosities and the buildup of oxidation products in Example 5 and Comparison 2, one can see that the antioxidant of the present invention definitely retards oxidative decomposition of an alkoxysilane cluster base fluid.

EXAMPLE 6

Example 6 describes the oxidative stability test on inhibited silicone oil. Example 4 was repeated, but dimethylsilicone oil of 100 cst at 25° C. viscosity was used, inhibited with 0.6% by weight of the inhibitor prepared in Example 1.

After 16 hours at 230° C., the viscosity increased from 104.5 cst for the formulated fluid (at 25° C.) to 113.05 cst (at 25° C.) which is an 8.7% increase.

Traces of volatiles (0.02%) were found in the trap.

COMPARISON 3

This was the control experiment to Example 6, using identical equipment but uninhibited commercial silicone oil of 100 cst viscosity at 25° C.

During the 16 hours heating at 230° C., the material gelled. Polymeric formaldehyde was found in the trap and connecting tube. Comparing the increase in viscosities and the buildup of oxidation products (e.g., formaldehyde) in Example 6 and Comparison 3, one can see that the antioxidant of the present invention definitely retards oxidative decomposition in a silicone oil base fluid.

What is claimed is:

1. A 4-hydroxyphenyl anilino alkoxysilane having the formula

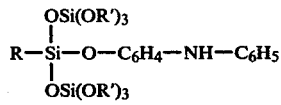

wherein R is hydrogen or a lower alkyl group having from 1 to 4 carbon atoms and each R' is individually selected from an alkyl group having from 3 to 12 carbon atoms, with the proviso that at least a majority of said R' radicals are stearically hindered alkyl groups.

2. The compound of claim 1 wherein R is a lower alkyl group having 1 to 4 carbon atoms.

3. The compound of claim 2 wherein R is methyl.

4. The compound of claim 1 wherein each R' is selected from sterically hindered alkyl groups having from about 4 to about 8 carbon atoms.

5. The compound of claim 4 wherein each R' is a sec-butyl radical.

6. The compound of claim 5 wherein R is methyl.

7. An oxidation-inhibited functional fluid composition comprising a base fluid component and an effective oxidation-inhibiting amount of a 4-hydroxyphenyl anilino alkoxysilane having the formula formula

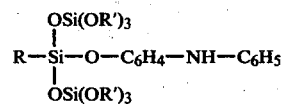

8. The functional fluid composition of claim 7 wherein said base fluid component comprises a shielded polysilicate compound.

9. The functional fluid composition of claim 7 wherein R is methyl and each R' is sec-butyl radical.

10. The functional fluid composition of claim 7 wherein said base fluid component comprises an alkoxysilane cluster compound.

11. The functional fluid composition of claim 7 wherein said base fluid component comprises a silicone oil.

12. A diffusion pump oil comprising a base fluid component comprising a shielded polysilicate compound and an effective oxidation-inhibiting amount of a 4-hydroxyphenyl anilino alkoxysilane as defined in claim 1.

13. The diffusion pump oil of claim 12 wherein said base fluid component comprises an alkoxysilane cluster compound.

* * * * *